United States Patent
Imam et al.

(10) Patent No.: US 10,329,623 B2
(45) Date of Patent: Jun. 25, 2019

(54) SYNTHETIC TISSUE CONTROLS AND SYNTHETIC TISSUE MICROARRAY CONTROLS

(71) Applicant: SLMP, LLC, McKinney, TX (US)

(72) Inventors: Syed Ashraf Imam, North Hollywood, CA (US); Mark Lee Rees, Huntington, NY (US)

(73) Assignee: SLMP, LLC, McKinney, TX (US)

( * ) Notice: Subject to any disclaimer, the term of this patent is extended or adjusted under 35 U.S.C. 154(b) by 121 days.

(21) Appl. No.: 14/880,450

(22) Filed: Oct. 12, 2015

(65) Prior Publication Data

US 2017/0059456 A1    Mar. 2, 2017

Related U.S. Application Data

(60) Provisional application No. 62/211,530, filed on Aug. 28, 2015.

(51) Int. Cl.
| | | |
|---|---|---|
| G01N 33/483 | (2006.01) | |
| C12Q 1/6886 | (2018.01) | |
| G01N 33/52 | (2006.01) | |
| G01N 33/574 | (2006.01) | |

(52) U.S. Cl.
CPC .......... C12Q 1/6886 (2013.01); G01N 33/52 (2013.01); G01N 33/57492 (2013.01); C12Q 2600/158 (2013.01); G01N 33/4833 (2013.01)

(58) Field of Classification Search
None
See application file for complete search history.

(56) References Cited

U.S. PATENT DOCUMENTS

| 6,517,830 B1 * | 2/2003 | Lollar | C07K 14/755 |
|---|---|---|---|
| | | | 424/93.21 |
| 2003/0109034 A1 | 6/2003 | Liao et al. | |
| 2004/0005559 A1 * | 1/2004 | Loring | C07H 21/04 |
| | | | 435/6.16 |
| 2004/0062753 A1 * | 4/2004 | Rezania | A61L 27/3847 |
| | | | 424/93.7 |
| 2004/0069699 A1 | 5/2004 | Ingram | |
| 2004/0096966 A1 | 5/2004 | Ingram | |
| 2006/0041385 A1 | 2/2006 | Bauer et al. | |
| 2009/0117653 A1 * | 5/2009 | Kirshner | C12N 5/0693 |
| | | | 435/378 |
| 2009/0245610 A1 | 10/2009 | Can et al. | |

FOREIGN PATENT DOCUMENTS

| WO | 1997018296 | 5/1997 |
|---|---|---|
| WO | 2007092571 | 8/2007 |

OTHER PUBLICATIONS

Goodwin et al. In Vitro Cell Dev Biol. 1992. 28A:47-60.*
Subik et al. Breast Cancer: Basic and Clinical Research. 2010. 4:35-41.*
Lattrich et al. Oncology Reports. 2008. 19:811-817.*
ISR/WO for PCT/US2016/048217 dated Nov. 4, 2016.

* cited by examiner

*Primary Examiner* — Joseph G. Dauner
(74) *Attorney, Agent, or Firm* — McGuireWoods, LLP

(57) ABSTRACT

The disclosed embodiments include methods to form STC and STMC for use in determining presence of cancer, and methods to detect presence of cancer. In one embodiment, A portion of a STC is stained. The STC includes normal cells and cancer cells of a type of cancer co-cultured based on at least one cell culturing factors. The at least one co-culture factors includes a type of the cancer cells being cultured, a ratio of the cancer cells to the normal cells being co-cultured, seeding density of the normal cells and the cancer cells being co-cultured, a type of cell growth supplement used to facilitate culturing the cells, and a concentration of the cell growth supplement used to facilitate co-culturing the cells. The stained portion is observed to determine presence of one or more biomarker types that indicate presence of cancer.

12 Claims, 5 Drawing Sheets

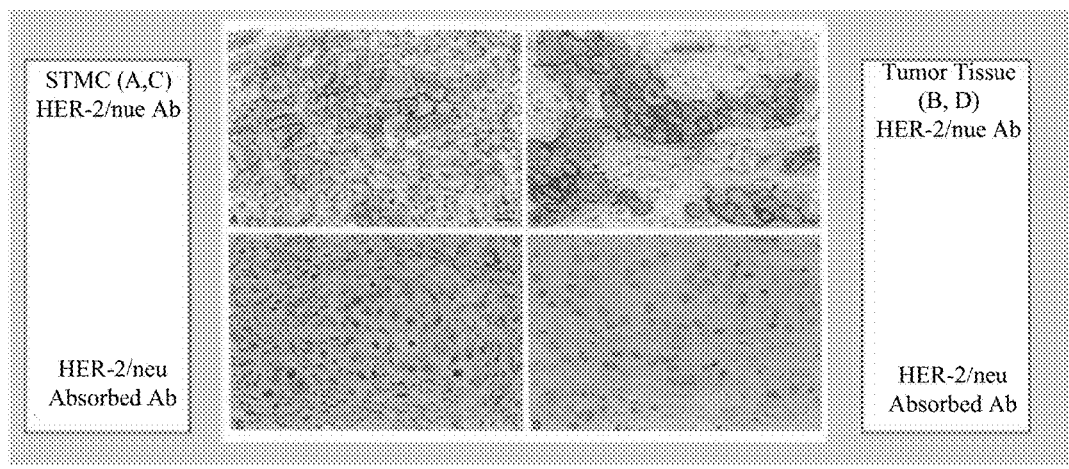

60% of top 100 abs covered by 4 ST TMAs

| Epithelial Tumors / carcinomas (keratin+) | Mesenchymal Tumor (vimentin+) (keratin usually negative, except where noted) |
|---|---|
| Breast<br>  EMA<br>  Brst2 (GCDFP-15)<br>  ER/PR<br>  Her-2/ neu (c-erb B-2)<br>  CK7<br>Lung<br>  Surfactant apoA<br>  TTF1<br>  p60<br>  p40<br>Liver<br>  *Hepatocellular-*<br>  AFP<br>  HepPar1<br>  Low MW keratin (cam 5.2, 35bh11<br>  *Cholangio-*<br>  Villin<br>  High MW keratins (34be12)*<br>GI Tract<br>  COTA (colonic ovarian tumor antigen)<br>  CEA<br>  CK 20/<br>  Mismatch repair<br><br>Thyroid<br>  TGB<br>  Calcitonin<br>  TTF-1<br>Prostate<br>  PSA<br>  PSMA<br>  Racemase<br>Renal<br>  RCC - renal tubular ag (gp200)<br>  CD10<br>  PAX8<br>Bladder<br>  Uropiakin III<br>Ovary<br>  OC-125<br>  WT-1 (serous)<br>  Mesothelin (serous)<br>Neuroendocrine Tumors (5)<br>  NSE, Synaptophysin, Leu, 7, Chromogranin | Rhabdomyosarcoma<br>  Muscle specific actin (HHF-35)<br>  Sarcomeric actin (asr-1)<br>  Desmin<br>  Myogenin<br>  MyoD1<br>  Myoglobin<br>Leiomyosarcoma<br>  Muscle specific actin (HHF-35)<br>  Smooth muscle actin (1A4)<br>  Desmin<br><br>GI stromal tumor (Chs. 10, 12)<br>  CD117 (c-kit)<br>  CD34<br>  DOG1<br><br>Endothelial Tumors<br>  Factor VIIIa (or von Willebrand's F)<br>  CD34<br>  CD31<br>  Ulex lectin<br><br>Liposarcoma)<br>  Type IV collagen only*<br>Dermatofibrosarcoma protuberans<br>  CD34<br>Fibrohistiocystic, fibroxanthoma,<br>  Lysozyme, F XIIIa, CD68<br><br>Synovial and epithelioid sarcoma<br>  Keratin, EMA<br><br>Histiocytic:- CD 68, lysozyme<br><br>Small round blue cell tumors**<br>  CD45 (lymphomas)<br>  CD99, Myogenin, WT-1<br>  NF (Neurofilament), FLI-1 |

Circles in left panel: Brst/fib, Lung/fib, Coln/fib

Circles in right panel: Mscl/fib, cd45/fib, endo/fib

FIG. 4
CONTINUED under defined and controlled conditions in suspension. As defined herein, "normal" cells include any non-tumor cells. Normal cells may be formed from stromal cells and other suitable cell types.

SYNTHETIC TISSUE CONTROLS AND SYNTHETIC TISSUE MICROARRAY CONTROLS

BACKGROUND

Pathology testing and clinical laboratory testing are important aspects of modern diagnostic and prognostic practices. Control samples are often used to maintain quality control (QC) for reproducibility of test results by immuno-histochemical (IHC) staining, in situ hybridization (ISH), and other methods of molecular analyses.

Some of the controls available for IHC staining and ISH staining of tumor tissues and other diseased tissues are cancer tissue-derived controls. However such types of controls are only available in very limited quantities, and once such controls are exhausted, replacement controls with the same characteristics may be unavailable. Other types of available controls are cancer cell lines-derived controls. However, such types of controls do not exhibit consistent patterns and levels of cellular expression of a given marker, or heterogeneity of said expression, which is ubiquitous to tumor tissues. As such, these controls have little or no morphological resemblance to actual tumor tissues.

SUMMARY

The disclosed embodiments provide methods for forming synthetic tissue controls and synthetic tissue microarray controls for IHC and ISH tests for cancer diagnosis and prognosis, as well as methods for determining presence of one or more types of cancer.

In accordance with an illustrative embodiment, a method for determining presence of at least one type of cancer is provided. The method includes staining a portion of a synthetic tissue control (STC). The STC includes normal cells and cancer cells of a type of cancer co-cultured based on at least one cell culturing factors. The at least one co-culture factors includes one or more of the following factors: A type of the cancer cell being cultured, a ratio of the cancer cells to the normal cells being co-cultured, seeding density of the cells being cultured, a type of cell growth supplement used to facilitate co-culturing the cells, and a concentration of the cell growth supplement used to facilitate co-culturing the cells. The method further includes observing the stained portion of the STC to determine a presence of one or more biomarker types, the one or more biomarker types indicating presence of the cancer cells.

In accordance with an illustrative embodiment, a method to form a synthetic tissue control for use in determining presence of cancer is provided. The method includes culturing cells comprising normal cells and cancer cells of a type of cancer based on at least one cell culturing factors. The at least one cell culturing factors includes a type the cancer cells being cultured, a ratio of the cancer cells to the normal cells being cultured, and seeding density of the cells being cultured.

In accordance with another illustrative embodiment, a synthetic tissue microarray is provided. The synthetic tissue microarray includes a plurality of STCs, each STC of the plurality of STCs includes normal cells and cancer cells of a type of cancer. The normal cells and the cancer cells are cultured based on at least one cell culturing factors. The at least one cell culturing factors includes a type of the cancer cells being cultured, a ratio of the cancer cells to the normal cells being cultured, seeding density of the normal cells and cancer cells being cultured, and a type of cell growth supplement used to facilitate culturing and growth of the normal cells and cancer cells.

Additional details of the disclosed embodiments are provided below in the detailed description and corresponding drawings.

BRIEF DESCRIPTION OF THE DRAWINGS

Illustrative embodiments of the present invention are described in detail below with reference to the attached figures, which are incorporated by reference herein, and wherein:

FIG. 2A illustrates an image of synthetic tissue containing breast cancer cells, which has been stained with a specific antibody to HER-2/nue to illustrate presence of HER-2/nue expression in accordance with one embodiment.

FIG. 2B illustrates an image of breast tumor tissue, which has been stained with a specific antibody to HER-2/nue to illustrate presence of HER-2/nue expression in accordance with one embodiment.

FIG. 2C illustrates an image of the synthetic tissue of FIG. 2A which has been stained with pre-absorbed antibody HER-2/nue as a test of specificity of the stain in accordance with one embodiment.

FIG. 2D illustrates an image of the breast tumor tissue of FIG. 2B which has been stained with pre-absorbed antibody HER-2/nue as a test of specificity of the stain in accordance with one embodiment.

Figure 1:
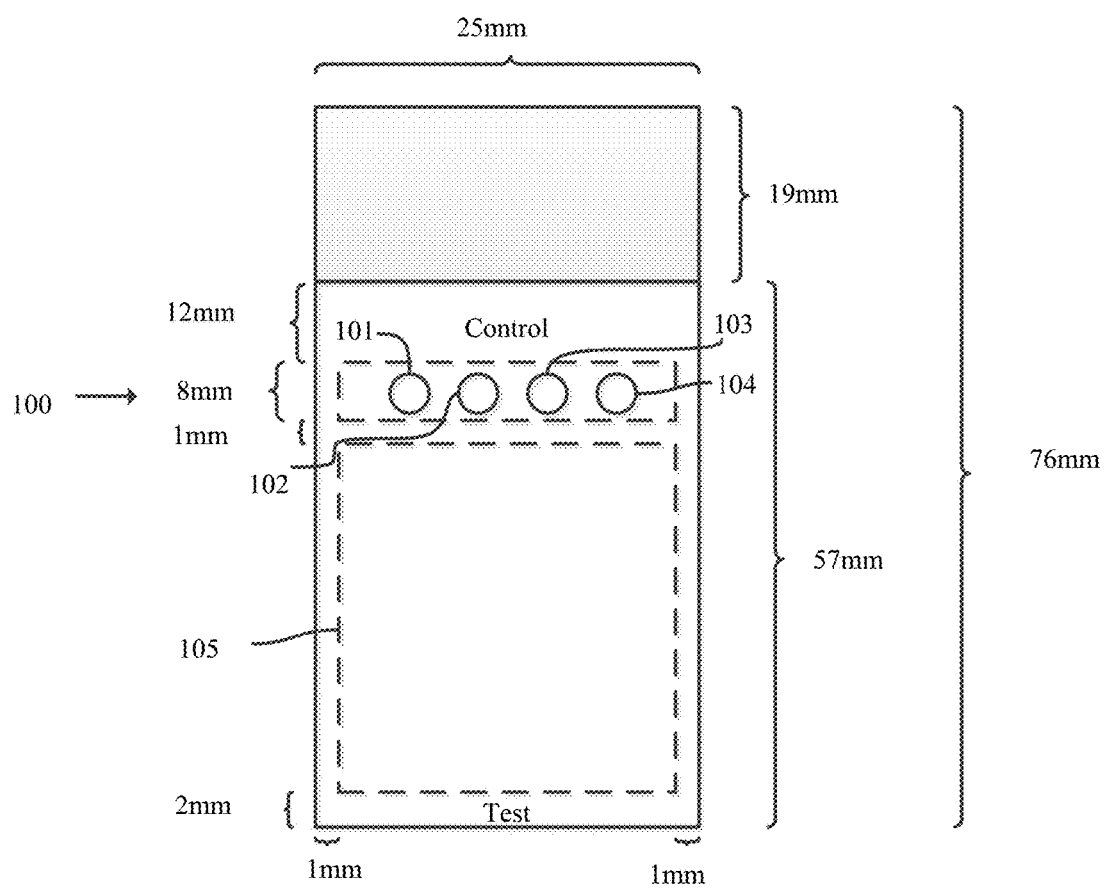
FIG. 1 is an illustration of a synthetic tissue microarray that includes four controls in accordance with one embodiment.

The illustrated figures are only exemplary and are not intended to assert or imply any limitation with regard to the environment, architecture, design, or process in which different embodiments may be implemented.

DETAILED DESCRIPTION

A 3-D Synthetic tissue control (STC) is generated by co-culturing normal cells and a type of cancer cells under defined and controlled conditions in suspension. As defined herein, "normal" cells include any non-tumor cells. Normal cells may be formed from stromal cells and other suitable cell types.

The STC reproducibly exhibits expected patterns and levels of tumor tissue associated cellular and extracellular (ECM) markers and architecture with close resemblance to tumor tissue. Examples of the close resemblance between STCs and tumor tissues are illustrated in FIGS. 2A-2D and FIGS. 3A-3E. 3-D Synthetic tissue microarray controls (STMC) are constructed from multiple STCs. In a preferred embodiment, STC and STMC are prepared as formalin-fixed and paraffin-embedded (FFPE) blocks or precut into sections for various markers used in pathology testing laboratories. Examples of compatible markers include various markers discussed in detail in the below description, as well as illustrated in the figures. The STC and STMC blocks and sections can be used as both positive and negative controls for IHC staining and ISH staining of tumor tissue and other diseased tissues. The processes for forming STCs and STMCs and using the STCs and STMCs to detect presence of cancer are provided in detail in the paragraphs below.

Cell Culture of STC and STMC

STCs are cultured in an approximately zero gravity culture, usually in the form of a formalin-fixed and paraffin-embedded (FFPE) cell block, where each STC contains a type of cancer cells and stromal cells. In some embodiments, cancer cells and normal stromal cells are separately cultured in cell-culture flasks. In one of such embodiments, a DNase of approximately 5 microgram per milliliter of cell culture medium is added to each cell-culture flask that contains either cancer cells or normal stromal cells. The addition of DNase prevents clumping of the harvested cancer cells or normal stromal cells from the cell-culture flasks. As a result, cell counts of the cancer cells and/or the normal stromal cells may be accurately determined and un-clumped cancer cells and normal stromal cells may be harvested.

In some embodiments, two or more cell-types (i.e., cancer cells and normal stromal cells) are co-cultured under stringently defined conditions and within a controlled environment. In one of such embodiments, a DNase of approximately 5 microgram per milliliter of cell culture medium is added to each cell culture bag containing cancer cells and normal stromal cells, where the cell culture bag is mounted on a bioreactor in a $CO_2$-incubator during the co-culturing process. The addition of the DNase facilitates cells to remain in an un-clumped condition in suspension during co-culture. More particularly, the addition of DNase facilitates the normal stromal cells to remain un-clumped, and thus allows the normal stromal cells to form a homogenous core. Further, the addition of DNase facilitates the cancer cells to remain un-clumped, and thus facilitates un-clumped cancer cells to invade the homogenous core. In another one of such embodiments, a Fibronectin of approximately 1 microgram per milliliter of the cell culture medium is added on the first day to co-culture in each cell culture bag containing the cancer cells and the normal stromal cells. In such embodiment, the addition of Fibronectin facilitates formation of basement membrane-like structures during an early phase of growth of the co-culture cells. Further, the addition of the Fibronectin facilitates an improved contact between the co-cultured cancer cells and the normal stromal cells. The formation of the basement membrane-like structures facilitates the co-cultured cells to resemble actual tumor tissue.

In a preferred embodiment, the cancer cells and the stromal cells are co-cultured in an approximately zero gravity environment for a period of eight to twelve days. Furthermore, the cancer cells and the stromal cells are co-cultured in a cell culture chamber configured to maintain a concentration of $CO_2$ and temperature inside and outside the chamber at levels based on at least one cell culturing factors to allow the cells to develop characteristics that are similar to or identical to actual tumor tissue. A motorized rotating device holds and slowly spins the cell culture chambers at a speed that is based on the at least one cell culturing factors to allow the cells to develop characteristics similar to or identical to characteristics of actual tumor tissue.

Cell culturing factors include, but are not limited to, the type of cancer cells being cultured, the ratio of the cancer cells to the stromal cells, seeding density of the cells being cultured, and concentration and type of cell growth supplement used to facilitate culturing the cells to develop characteristics that are similar to or identical to actual tumor tissue. In one example embodiment, a ratio of the cancer cells for a breast cancer cell line (MCF.7) to the normal stromal cell (fibroblast) is 1 in 99.8, respectively, to produce the STC. Additionally, 10 micrograms of insulin are used as a growth factor supplement to facilitate growth of the MCF 7. Furthermore, the seeding density of MCF.7 cancer cells is 18,750 per milliliter, whereas that of the fibroblast 187,876 per milliliter. Similarly, STMCs are also cultured based on the above described process. In one embodiment, STC and STMC are cultured based on one of the above-identified factors. In another embodiment, STC and STMC are cultured based on two of the above-identified factors. In a further embodiment, STC and STMC are cultured based on three of the above-identified factors. In a further embodiment, STC and STMC are cultured based on all of the above-identified factors.

STC and STMC are cultured, based on at least one of the previously stated cell culturing factors, to provide control 'faux' tissues having known patterns and levels of expression of various markers, including proteins, RNAs, DNAs and other components of interest, for diagnosis, prognosis, and selection of patients for a particular specific/targeted therapy. STC and STMC may be cultured for standard expression of markers employed in IHC as diagnostic and predictive markers for treatment response, exemplified by tests for Epidermal Growth Factor Receptor-2 (HER-2/nue), estrogen receptor (ER), progesterone receptor (PR), Ki-67, and other types of suitable diagnostic and predictive markers for treatment response. STC and STMC may further be cultured for standard expression of markers that are employed in IHC as predictive markers to treatment response, exemplified by tests for HER-2/nue, Met 4, as well as other types of suitable predictive markers for treatment response. Furthermore, STC and STMC may also be cultured or standard expression of markers employed in immunofluorescence techniques.

STC and STMC may also be cultured to provide a consistent level of expression when observed via a fluorescence in situ hybridization (FISH) based technique for RNA and/or DNA markers. In certain embodiments, the expression may include expression levels of RNA translocations. In other embodiments, the expression may include expression levels of DNA mutations. STC and STMC may also be cultured to provide a consistent level of expression when observed via a chromogenic in situ hybridization (CISH) based technique for RNA and/or DNA markers. In certain embodiments, the expression may include expression levels of RNA translocations and/or DNA mutations. As such, an almost limitless range of biomarkers may be provided by selection of cell lines that are employed to make the STC or STMC.

STC and STMC may be cultured, based on at least one of the previously stated cell culturing factors, to consistently provide various levels of expressions of biomarkers used in IHC and ISH staining. In some embodiments, STC and STMC are cultured to provide high expression (HE or 3+) of biomarkers used in IHC and ISH staining. In other embodiments, STC and STMC are cultured to have medium expression (ME or 2+) of biomarkers used in IHC and ISH staining. In further embodiments, STC and STMC are cultured to have low expression (LE or 1+) of biomarkers used in IHC and ISH staining.

Processing and Embedding STC and STMC

The cultured STC is processed and then embedded. In one embodiment, the diameter of the cultured STC is approximately 0.05 cm. In another embodiment, the diameter of the cultured STC may be within a range of 0.01-0.05 cm. Contrary to the STC, the tissue specimen may have a diameter of 2-3 cm. Given the size of the cultured STC, a processing and an embedding device having a mesh with pore size approximately 0.001 cm is used to hold the tissue specimen during the embedding process. In another embodiment, the pore size of the embedding device is within a range of 0.001-0.005 cm. A plurality of cultured STCs that provide a desired level of expression of desired biomarkers is embedded to form a STMC.

Staining STC and STMC

A section from each block of the embedded STC is evaluated by IHC staining techniques to identify individual constructs. In some embodiments, the individual constructs in the embedded STC represent 50 to 60% from the total of approximately 500 individual constructs with the desired combination of cancer cells and normal stromal cells and the invasion of normal stromal cell core by the cancer cells. In other embodiments, the individual constructs in the embedded STC represent 80% from the total of 500-600 individual constructs with the desired combination of cancer cells and normal stromal cells and the invasion of normal stromal cell core by the cancer cells. In some embodiments, only constructs with characteristics that are similar or identical to actual tumor tissue are selected as STC.

Individual constructs from each block containing a certain combination of co-cultured cell types with characteristics that are similar or identical to actual tumor tissue are mechanically removed from the original block and are used to construct a STMC. The STMC is constructed to include a plurality of types of cancer cells with varying levels and patterns of expression of markers of interest. The STC and STMC may be viewed by laboratory operators via a variety of devices such as microscopes, whole slide imaging (WSI) devices, and other suitable devices for observing expressions of biomarkers.

FIG. 1 is an illustration of a synthetic tissue microarray 100 that includes four STCs 101, 102, 103, and 104 in accordance with one embodiment. In the embodiment illustrated in FIG. 1, controls 101, 102, 103, and 104 are placed proximate to test tissue 105 on the same histologic slide. The controls 101, 102, 103, and 104 and the test tissue 105 are stained with one or more stains for different types of biomarkers.

In some embodiments, the synthetic tissue microarray 100 is stained to observe for expression of markers employed in IHC as diagnostic markers and predictive markers for treatment response. In other embodiments, the synthetic tissue microarray 100 is stained to observe for expression of markers employed in IHC as predictive markers for treatment response. In further embodiments, the synthetic tissue microarray 100 is stained and observed via a FISH technique, for a level of expression of RNA and DNA markers. In further embodiments, the synthetic tissue microarray 100 is stained and observed via a CISH technique, for a level of expression of RNA and DNA markers.

In some embodiments, the synthetic tissue microarray 100 provides positive controls for at least one type of cancer. In other embodiments, some controls of the synthetic tissue microarray 100 provide positive controls while other controls of the synthetic tissue microarray 100 provide negative controls. The synthetic tissue microarray 100 may be cultured to provide high expression, medium expression, or low expression of the markers. Although the embodiment illustrated in FIG. 1 includes four controls 101, 102, 103, and 104, the synthetic tissue microarray 100 may be formed from a different number of controls. A laboratory operator may examine the synthetic tissue microarray 100 under a variety of devices such as microscopes and WSI devices to compare the stained controls with the stained test tissue to determine presence or absence of expression of markers in test tumor tissues.

FIG. 2A illustrates an image of synthetic tissue containing breast cancer cells in accordance with one embodiment. FIG. 2B illustrates an image of breast tumor tissue in accordance with one embodiment. The synthetic tissue illustrated in FIG. 2A has been cultured under conditions described herein. As shown in FIGS. 2A and 2B, the synthetic tissue containing breast cancer cells and the actual breast tumor tissues exhibit significantly similar characteristics.

FIG. 2C illustrates an image of the synthetic tissue of FIG. 2A after the synthetic tissue is stained with pre-absorbed antibody to HER-2/nue to illustrate a specificity of the stain for HER-2/nue marker in accordance with one embodiment. FIG. 2D illustrates an image of the breast tumor tissue of FIG. 2B after the tumor tissue is stained with pre-absorbed antibody to HER-2/nue to illustrate a specificity of the stain for HER-2/nue marker in accordance with one embodiment. As shown in FIGS. 2C and 2D, the stained synthetic tissue and the stained tumor tissue exhibit significantly similar characteristics, which allow the synthetic tissue to be used as a control for standard expression of markers that are employed in IHC as a diagnostic marker or as a predictive marker for treatment response such as HER-2/nue. Other examples of expression of markers that are employed in IHC as predictive markers for treatment response include Met 4, as well as other suitable diagnostic markers or predictive markers for treatment response. In further embodiments, the synthetic tissues illustrated in FIGS. 2A and 2C may also provide a level of expression of RNA and DNA markers when observed via a FISH technique. In further embodiments, the synthetic tissues illustrated in FIGS. 2A and 2C may also provide a level of expression of RNA and DNA markers when observed via a CISH technique.

Figures 3A, 3B, 3C, 3D, 3E, 3F:
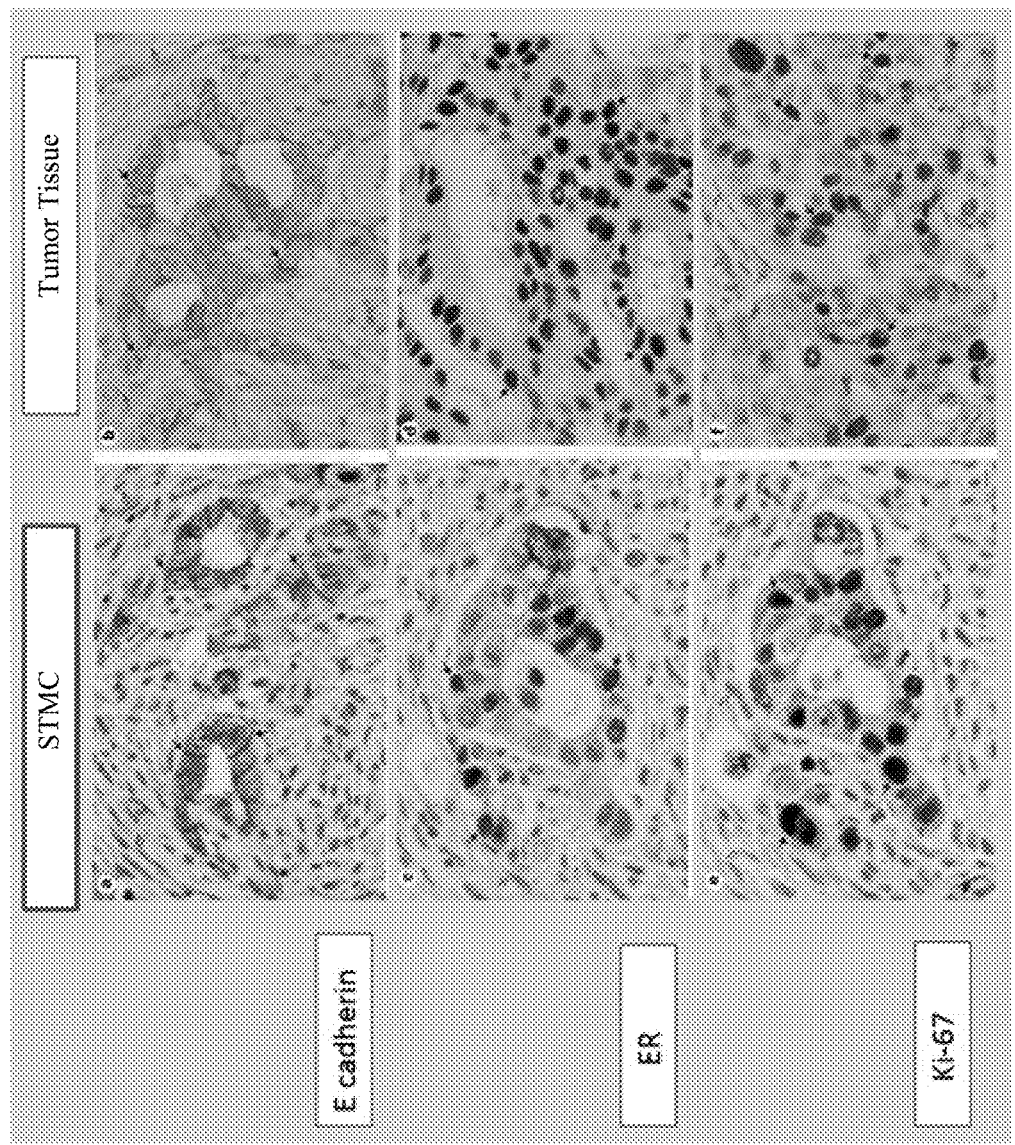
FIG. 3A illustrates an image of synthetic tissue stained to illustrate presence of E Cadherin marker in accordance with one embodiment.
FIG. 3B illustrates an image of breast tumor tissue stained to illustrate presence of E Cadherin marker in accordance with one embodiment.
FIG. 3C illustrates an image of synthetic tissue stained to illustrate presence of Estrogen Receptor marker in accordance with one embodiment.
FIG. 3D illustrates an image of breast tumor tissue stained to illustrate presence of Estrogen Receptor marker in accordance with one embodiment.
FIG. 3E illustrates an image of synthetic tissue stained to illustrate presence of a cell proliferation (Ki-67) marker in accordance with one embodiment.
FIG. 3F illustrates an image of breast tumor tissue stained to illustrate presence of a cell proliferation (Ki-67) marker in accordance with one embodiment.

FIG. 3A illustrates an image of synthetic tissue stained to illustrate presence of E Cadherin marker in accordance with one embodiment. FIG. 3B illustrates an image of breast tumor tissue stained to illustrate presence of E Cadherin marker in accordance with one embodiment. FIG. 3C illustrates an image of synthetic tissue stained to illustrate presence of Estrogen Receptor marker in accordance with one embodiment. FIG. 3D illustrates an image of breast tumor tissue stained to illustrate presence of Estrogen Receptor marker in accordance with one embodiment. FIG. 3E illustrates an image of synthetic tissue stained to illustrate presence of a proliferation (Ki-67) marker in accordance with one embodiment. FIG. 3F illustrates an image of breast tumor tissue stained to illustrate presence of a proliferation (Ki-67) marker in accordance with one embodiment.

The synthetic tissues illustrated in FIGS. 3A, 3C, and 3E have been cultured under conditions described herein. As shown in FIGS. 3A-3F, the synthetic tissues and the stained tumor tissues exhibit significantly similar characteristics, which allow the synthetic tissues to be employed in IHC as diagnostic markers and predictive markers for treatment response, exemplified by tests for E Cadherin, ER, progesterone receptor, and Ki-67, as well as tests for other suitable types of diagnostic markers and predictive markers for treatment response. In other embodiments, the synthetic tissues illustrated in FIGS. 3A, 3C, and 3E may also be used to provide for expressions of biomarkers employed in IHC as predictive markers for treatment response. In further embodiments, the synthetic tissues illustrated in FIGS. 3A, 3C, and 3E may also provide a level of expression of RNA and DNA markers when observed via a FISH technique. In further embodiments, the synthetic tissues illustrated in FIGS. 3A, 3C, and 3E may also provide a level of expression of RNA and DNA markers when observed via a CISH technique.

Figure 4:
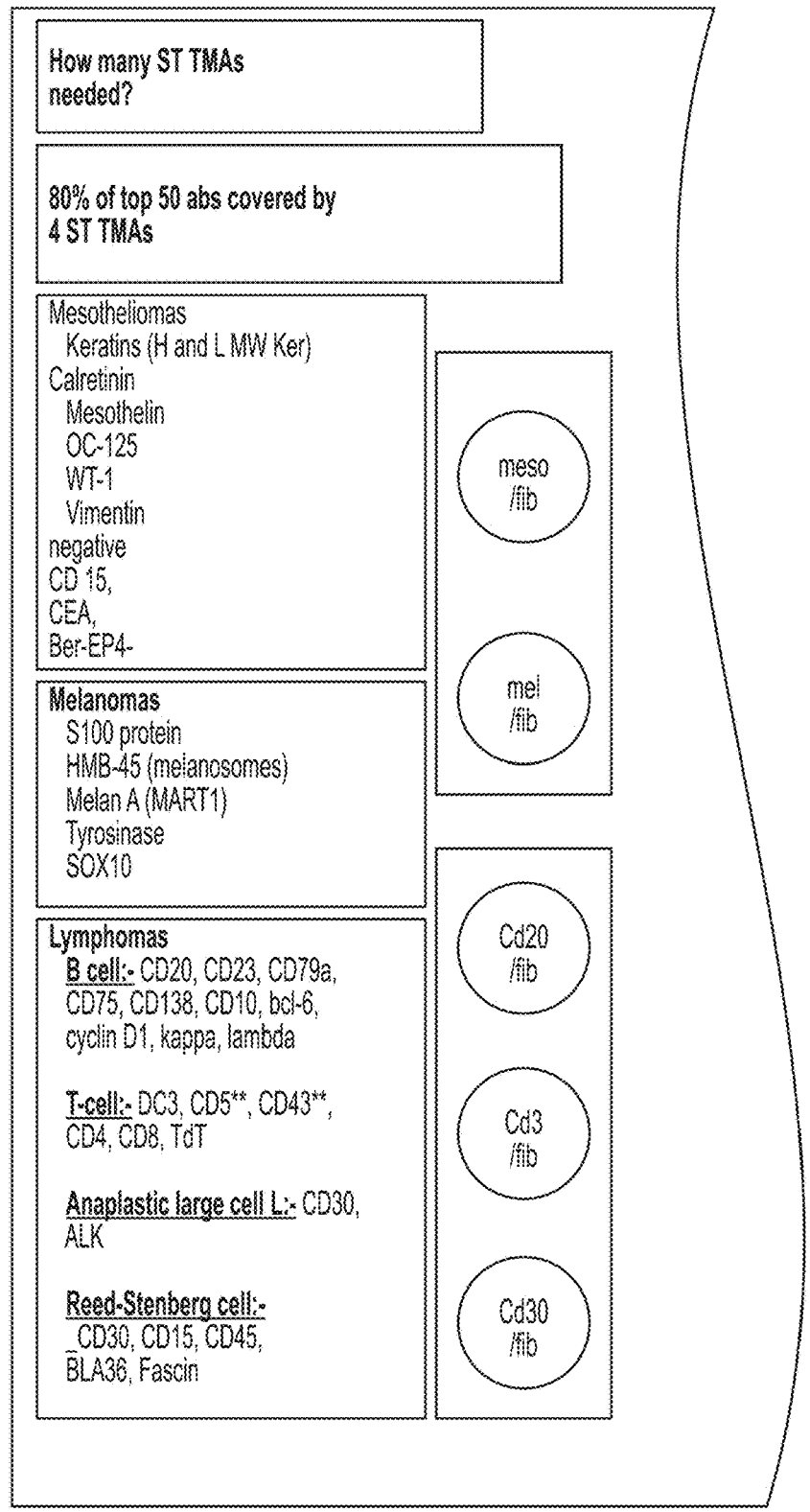
FIG. 4 illustrates examples of antibodies for detecting different types of cancers that are covered by the synthetic tissue controls and the synthetic tissue microarrays described herein, in accordance with one embodiment.

FIG. 4 illustrates examples of antibodies for detecting different types of cancers that are covered by the synthetic tissue controls and the synthetic tissue microarray controls described herein, in accordance with one embodiment. As illustrated in FIG. 4, STC and STMC can be used to test a variety of types of cancers including, but not limited to breast cancer, lung cancer, liver cancer, thyroid cancer, prostate cancer, colon cancer, cervical cancer, kidney cancer, ovarian cancer, melanoma cancer, brain cancer, leukemia, lymphomas as well as other types of cancers.

The above disclosed embodiments have been presented for purposes of illustration and to enable one of ordinary skill in the art to practice the disclosed embodiments, but is not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/blocks may be performed in parallel or out of sequence, or combined into a single step/block. The scope of the claims is intended to broadly cover the disclosed embodiments and any such modification.

As used herein, a "approximately zero gravity environment" is defined to include a zero gravity environment.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

What is claimed is:

1. A method to form a synthetic tissue control for use in determining presence of cancer, the method comprising:
   preparing an approximately zero gravity environment for cell culture;
   culturing cells comprising normal cells and cancer cells of a type of cancer in the approximately zero gravity environment and based on seeding density of the normal cells and the cancer cells being cultured; and
   adding approximately 5 micrograms of DNase per milliliter of cell culture medium to facilitate un-clumping of the normal cells and the cancer cells during co-culturing of the cells.

2. The method of claim 1, wherein culturing the cells comprises co-culturing the normal cells and the cancer cells in a cell culture chamber configured to maintain a concentration of $CO_2$ and temperature inside the cell culture chamber.

3. The method of claim 2, wherein culturing the cells further comprises maintaining the cell culture chamber in a motorized rotating device operable to:
   hold the synthetic tissue control; and
   spin the cell culture chamber at a predetermined speed during co-culturing of the cells.

4. The method of claim 3, further comprising:
   forming a homogenous core with un-clumped normal cells; and
   invading the homogenous core with un-clumped cells of the cancer cells.

5. The method of claim 1, further comprising adding Fibronectin to improve contact between the normal cells and the cancer cells.

6. The method of claim 1, wherein culturing the cells comprises culturing the cells in the approximately zero gravity environment for a period of 8-12 days.

7. The method of claim 1, wherein culturing cells comprising normal cells and cancer cells comprises culturing normal cells and breast cancer cells.

8. The method of claim 7, wherein a ratio of the breast cancer cells to the normal cells is approximately 1:99.8.

9. The method of claim 7, wherein the breast cancer cells are MCF.7 cancer cells.

10. The method of claim 9, wherein the seeding density of MCF.7 cancer cells is approximately 18,750 per milliliter.

11. The method of claim 1, wherein the seeding density of the normal cells is approximately 187,876 per milliliter.

12. The method of claim 1, further comprising staining the synthetic tissue control with a stain to observe one or more expressions of specific markers of the cancer cells.

* * * * *